(12) United States Patent
Putallaz et al.

(10) Patent No.: US 9,943,440 B2
(45) Date of Patent: Apr. 17, 2018

(54) DEVICE FOR HOLDING FOLDING AND INJECTING AN INTRAOCULAR LENS

(71) Applicant: ALTACOR LIMITED, Cambridge (GB)

(72) Inventors: Sebastien Putallaz, Sarnen (CH); Laurent Pivard, Bellignat (FR)

(73) Assignee: ALTACOR LIMITED, Cambridge (GB)

( * ) Notice: Subject to any disclaimer, the term of this patent is extended or adjusted under 35 U.S.C. 154(b) by 143 days.

(21) Appl. No.: 14/482,771

(22) Filed: Sep. 10, 2014

(65) Prior Publication Data

US 2014/0378987 A1 Dec. 25, 2014

Related U.S. Application Data

(63) Continuation of application No. 13/257,067, filed as application No. PCT/EP2009/053206 on Mar. 18, 2009, now Pat. No. 8,858,625.

(51) Int. Cl.
*A61F 9/007* (2006.01)
*A61F 2/16* (2006.01)

(52) U.S. Cl.
CPC .......... *A61F 9/00736* (2013.01); *A61F 2/167* (2013.01); *Y10T 29/49826* (2015.01)

(58) Field of Classification Search
CPC .... A61F 9/00736; A61F 2/167; A61F 2/1672; A61F 2/1675; A61F 2/1678; A61F 2/1664; A61F 2/1662; A61F 2/1681
See application file for complete search history.

(56) References Cited

U.S. PATENT DOCUMENTS 4,681,102 A * 7/1987 Bartell .................. A61F 2/1678 606/1
5,499,987 A * 3/1996 Feingold ............... A61F 2/1664 206/5.1

(Continued)

FOREIGN PATENT DOCUMENTS

CN 1602173 A 3/2005
EP 1 114 623 A1 7/2001

(Continued)

OTHER PUBLICATIONS

European Patent Office Communication mailed in the correspond EP Appliation No. 09 779 175.0 dated Oct. 1, 2013 (6 pages).

(Continued)

*Primary Examiner* — Jocelin Tanner
(74) *Attorney, Agent, or Firm* — Birch, Stewart, Kolasch & Birch, LLP

(57) ABSTRACT

An injector (1) for folding and injecting into the eye of a patient a flexible intraocular lens, the injector comprising an assembly of an injection nozzle (202), a lens compartment that holds an unfolded flexible intraocular lens (400) and is in communication with the injection nozzle, an injector body (3) communicating with the lens compartment and a plunger (2) that is inserted in the free end of the injector body, wherein lens compartment and injector body comprise a mechanism whereby the lens is first folded by forces compressing the lens in a non-axial direction in response to an axial movement of the plunger over a first distance and is subsequently expelled from the injector through the injection nozzle in response to an axial movement of the plunger over a second distance.

21 Claims, 12 Drawing Sheets

(56) References Cited

U.S. PATENT DOCUMENTS

| | | | |
|---|---|---|---|
| 6,334,862 B1* | 1/2002 | Vidal | A61F 2/1664 606/107 |
| 6,500,181 B1 | 12/2002 | Portney | |
| 2003/0139749 A1* | 7/2003 | Kikuchi | A61F 2/167 606/107 |
| 2004/0097956 A1* | 5/2004 | Oda | A61F 2/1664 606/107 |
| 2004/0117012 A1* | 6/2004 | Vincent | A61F 2/167 623/6.12 |
| 2004/0147938 A1* | 7/2004 | Dusek | A61F 2/1664 606/107 |
| 2005/0125000 A1* | 6/2005 | Tourrette | A61F 2/1678 606/107 |
| 2005/0283162 A1* | 12/2005 | Stratas | A61F 2/1664 606/107 |
| 2007/0000801 A1* | 1/2007 | Mauran | A61F 2/1664 206/438 |
| 2009/0318933 A1* | 12/2009 | Anderson | A61F 2/1664 606/107 |
| 2010/0106160 A1* | 4/2010 | Tsai | A61F 2/167 606/107 |

FOREIGN PATENT DOCUMENTS

| | | |
|---|---|---|
| EP | 1 958 593 A1 | 8/2008 |
| JP | 2004-528078 A | 9/2004 |
| JP | 2007-244570 A | 9/2007 |
| WO | 2010/048096 A1 | 4/2010 |

OTHER PUBLICATIONS

International Preliminary Report on Patentability dated Sep. 29, 2011, in PCT International Application No. PCT/EP2009/053206.
International Search Report dated Jan. 4, 2010, in PCT International Application No. PCT/EP2009/053206.

* cited by examiner

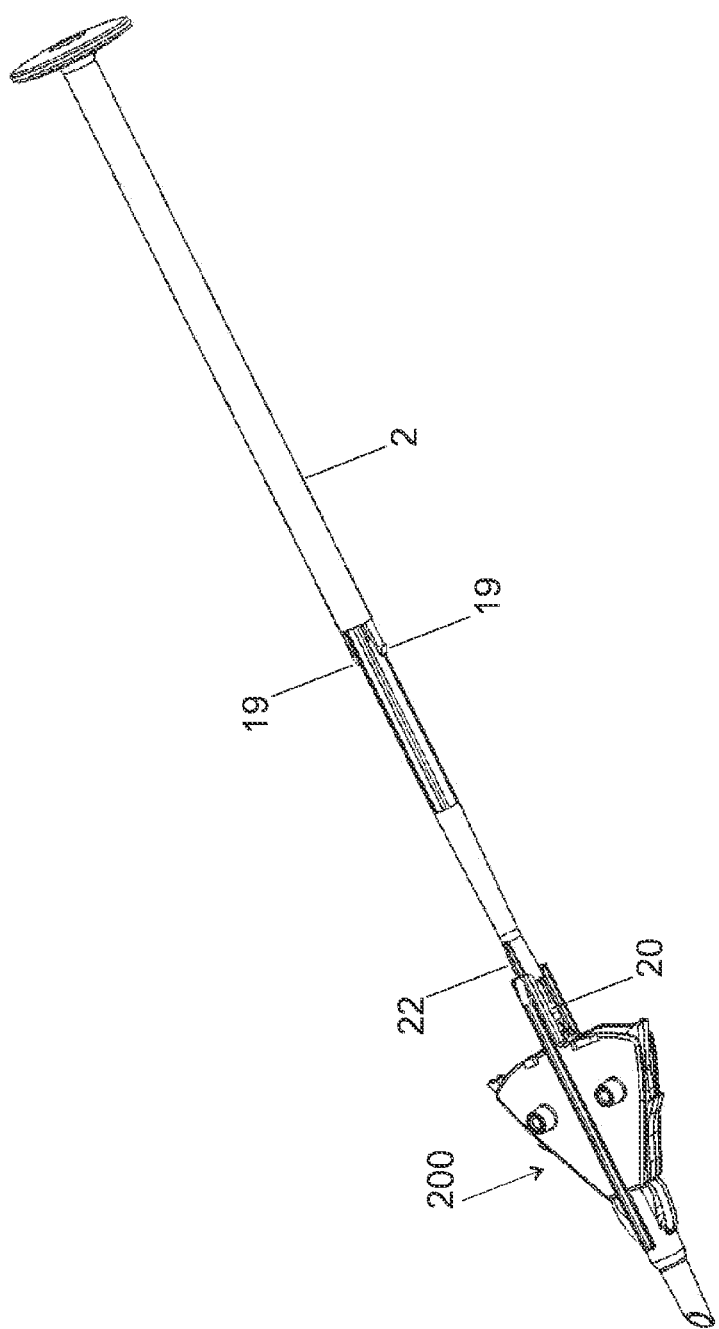

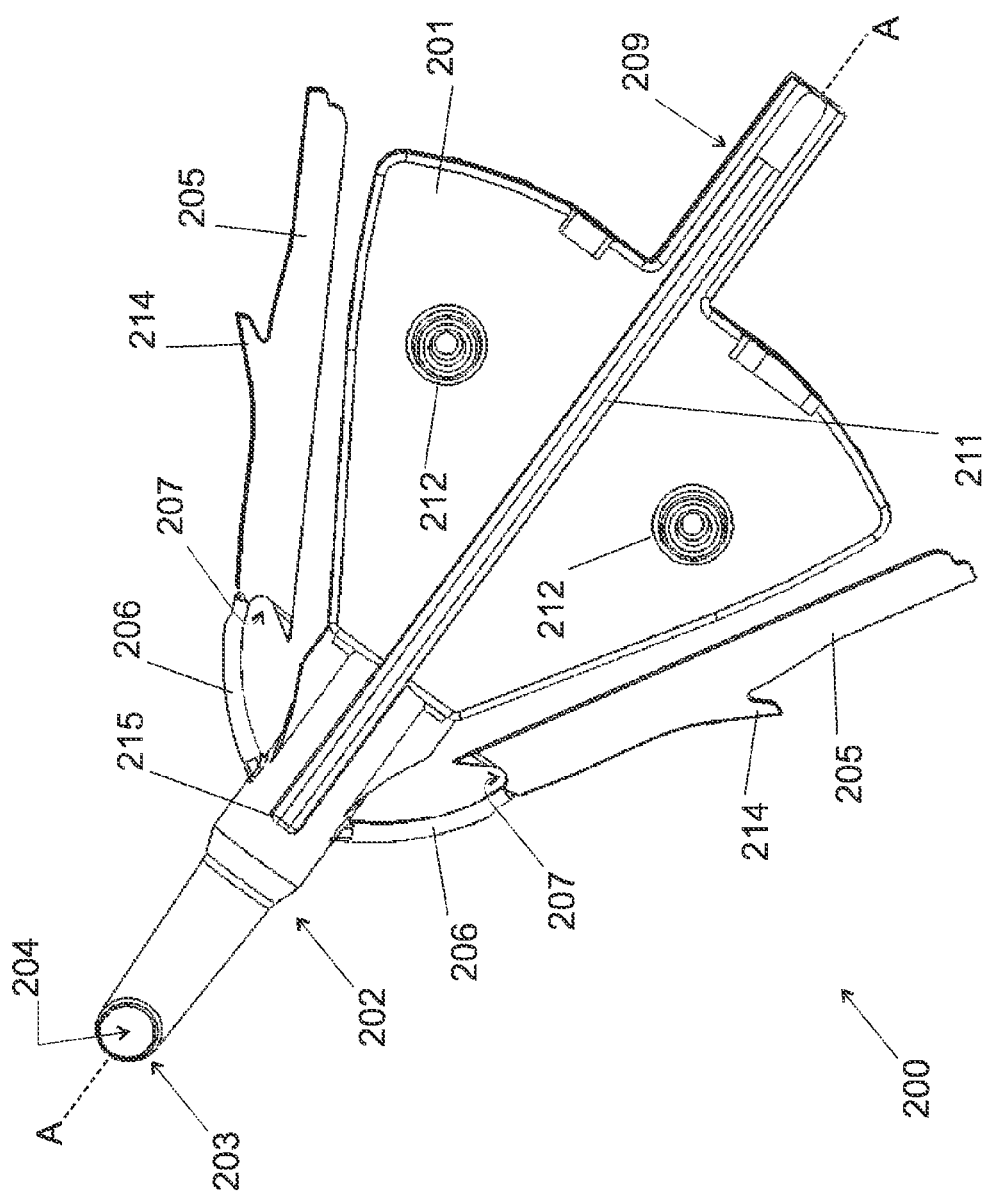

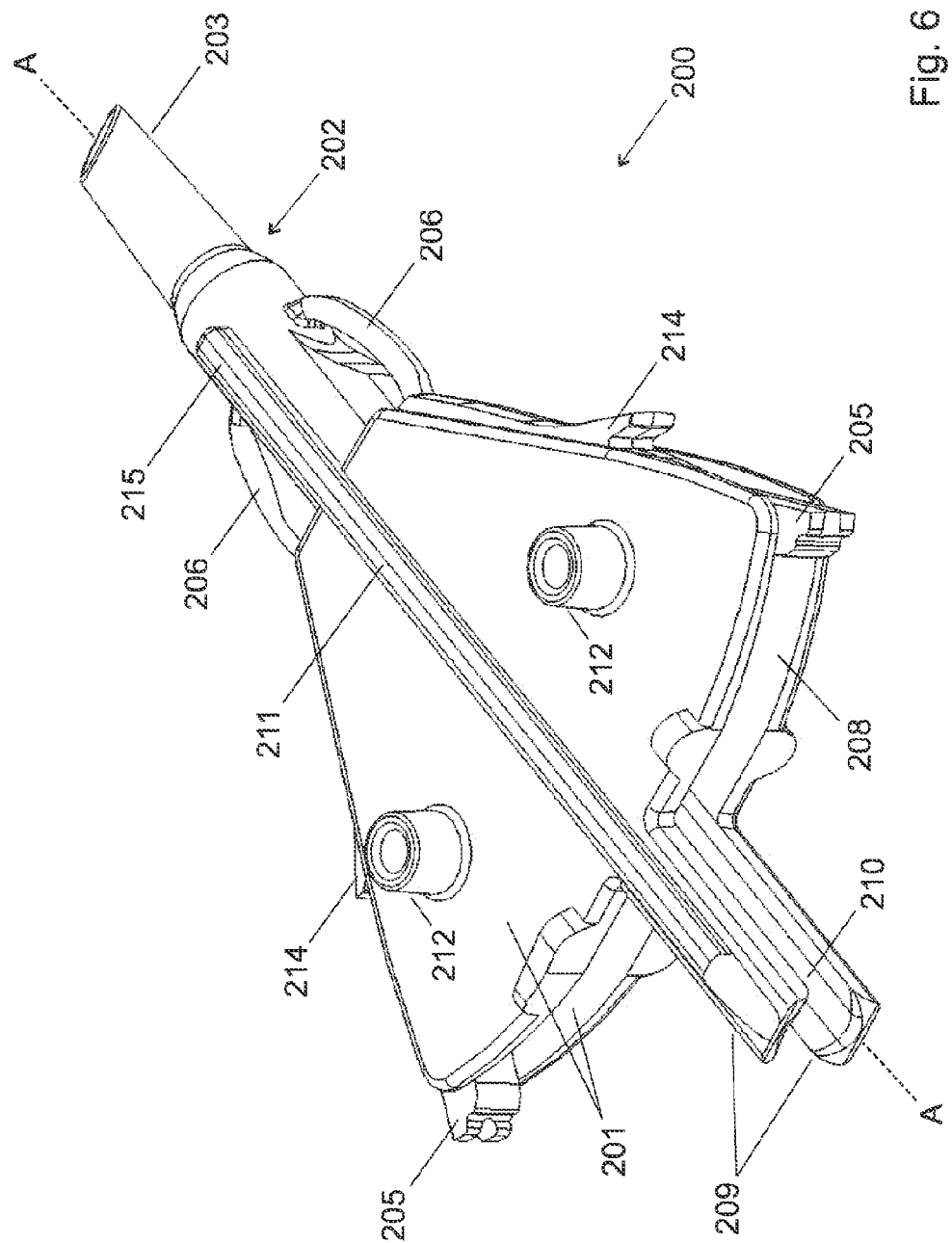

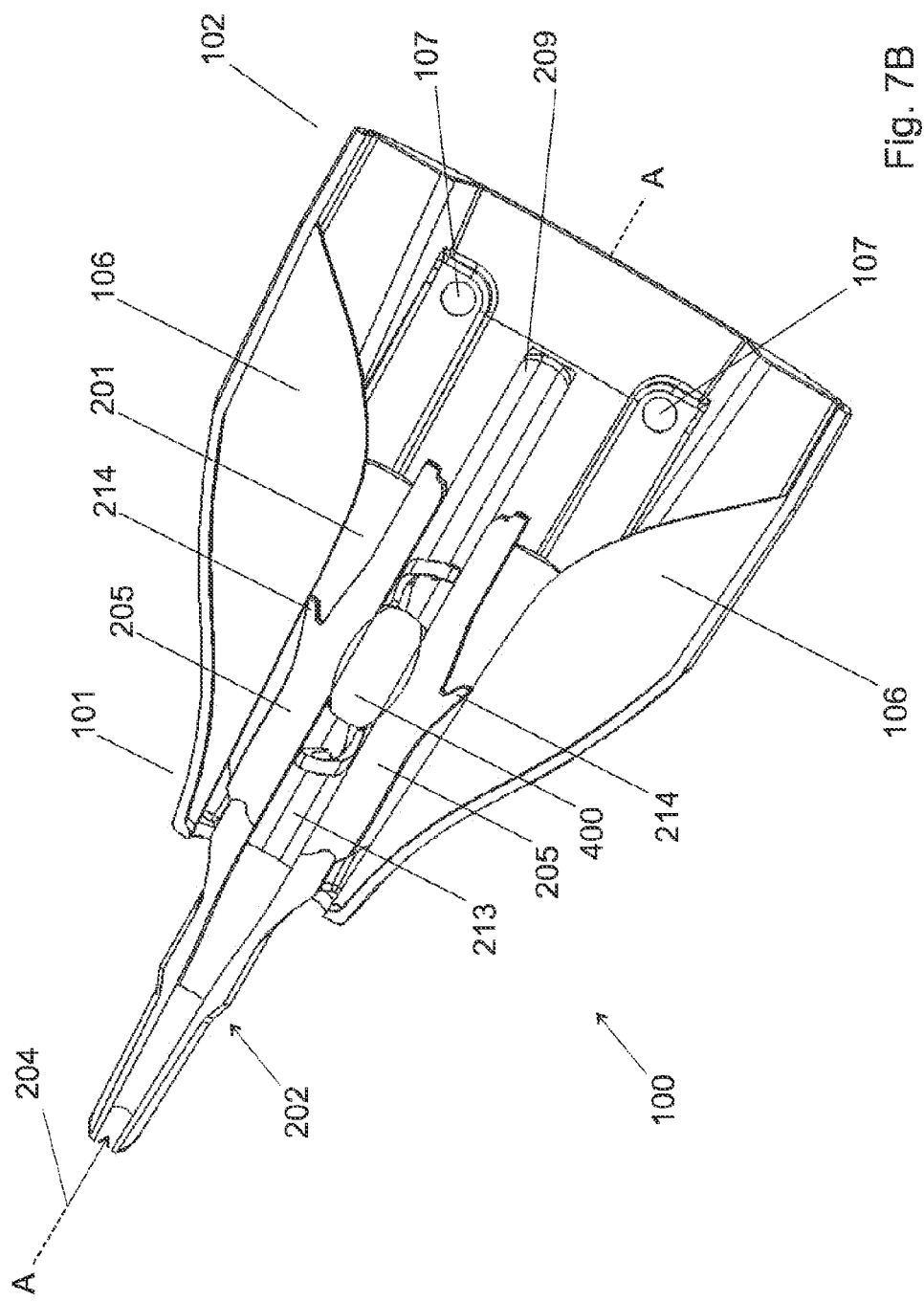

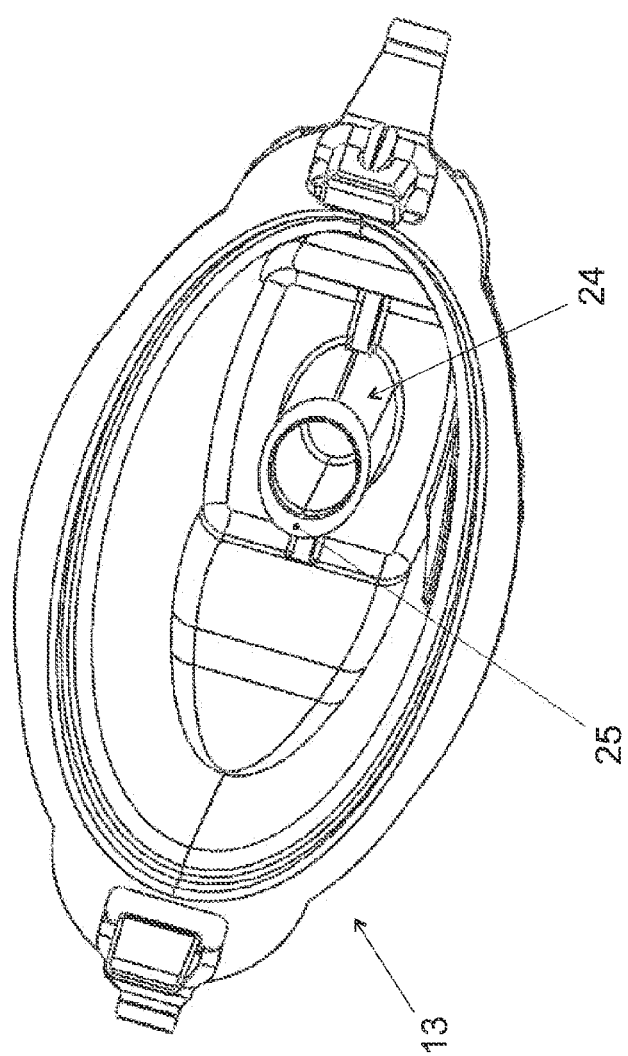

DEVICE FOR HOLDING FOLDING AND INJECTING AN INTRAOCULAR LENS

CROSS-REFERENCE TO RELATED APPLICATIONS

This application is a Continuation of copending application Ser. No. 13/257,067, filed on Nov. 30, 2011, which claims priority under to Application No. PCT/EP2009/053206, filed in WIPO on Mar. 18, 2008, all of which are hereby expressly incorporated by reference into the present application.

FIELD OF THE INVENTION

The invention relates to a device and a method for injecting a flexible intraocular lens which is ready to use, i.e. ready to be implanted by injection through an incision formed in the wall of a patient's eye.

DESCRIPTION OF RELATED ART

Flexible intraocular lenses are useful, for example, in a cataract operation in order to restore sight by a surgical procedure, which inserts into the eye such intraocular lens, which replaces the natural lens that has become opaque due to the cataract.

Flexible intraocular lenses are often made of hydrophilic material(s) such as, for example, hydrogel, acrygel or acrylic (the latter term deviating from its normal meaning), which materials are PMMA (polymethylmethacrylate) and/or HEMA (hydroxymethylmethacrylate), hydrated to more than 16%, in particular between 24% and 28%. U.S. Pat. No. 4,787,904 describes various examples of materials that may be used to produce hydrophilic lenses. These lenses need to be kept in a hydrated state for conservation.

Flexible intraocular lenses can also be made from silicone materials, having a higher refractive index than hydrophilic materials, or hydrophobic acrylic materials with low glass transition temperatures. The latter materials are desirable because they typically have a high refractive index and lenses made from them unfold more slowly and more controllably than silicone lenses. U.S. Pat. No. 7,157,538 describes such a high refractive index, acrylic material used for making hydrophobic flexible intraocular lenses.

Flexible intraocular lenses have the advantage of being able to be folded, allowing them to pass through incisions in the eye of small dimensions. However, the problem arising with these flexible lenses is precisely that of folding and manipulating them at the moment of the surgical act. U.S. Pat. No. 4,787,904 proposes to conserve a hydrophilic lens in a folded state in the injection device while being immersed in a conserving solution, the whole assembly being contained in a flexible packaging pocket. However, this method may not be used in practice, since a lens which has remained folded for a long period may retain a shape memory of the folded state and therefore does not regain its unfolded, functional shape after implantation.

As a result, hydrophilic lenses up to now have been conserved flat in sterilized rigid containers of conserving solution. At the moment of the surgical act, the surgeon removes the lens using a pincer, folds it (optionally with the aid of a folding device) or places it in a folding cartridge or in an injector and injects it into the eye. These manipulations are relatively complex and delicate, increasing the risk of contamination and damage to the lens.

U.S. Pat. No. 6,386,357 discloses a soft intraocular lens-folding device comprising a base member with a tapered slide groove portion, and a movable member comprising an elastically bendable pair of legs and a common base connecting the pair of legs. A soft intraocular lens is introduced in the lens-receiving portion of the movable member, the lens being clamped by wall portions. The lens is folded by moving the movable member into the groove portion in the base member, forcing the legs of the movable member to be drawn near to one another. This document does not disclose any means for injecting the folded lens.

U.S. Patent Publication No. 2005182419 discloses an injector for an intraocular lens comprising an injector housing with an intraocular lens disposed in the housing. The injector further comprises a lens carrier, which, in response to an actuator, engages and moves the lens within a narrowing injection nozzle in order to fold the lens. A plunger is then used to advance the folded lens and inject it into a patient's eye. Here, folding and injection of the lens cannot be achieved by a single, continuous movement of a plunger, adding complexity to the surgical procedure.

BRIEF SUMMARY OF THE INVENTION

The present invention is to provide a device and a method for injecting a flexible intraocular lens through an incision formed in the wall of a patient's eye, where the lens is reproducibly folded before it is injected.

The aims of the present invention are achieved, among others, by an injector for folding and injecting into the eye of a patient a flexible intraocular lens, the injector comprising an assembly of an injection nozzle, a lens compartment that holds an unfolded flexible intraocular lens and is in communication with the injection nozzle, an injector body communicating with the lens compartment and a plunger that is inserted in the free end of the injector body, wherein lens compartment and injector body comprise a mechanism whereby the lens is first folded by forces compressing the lens in a non-axial direction in response to an axial movement of the plunger over a first distance and is subsequently expelled from the injector through the injection nozzle in response to an axial movement of the plunger over a second distance.

In another embodiment of the lens injector of the invention, the lens compartment is integrated in the injector body.

In a particular embodiment of the invention, the injector comprises:

a) a hollow injector body comprising a distal flange and a proximal end piece comprising an opening for insertion of a plunger, b) a lens compartment consisting of a support guide and a lens support, the support guide consisting of an open hollow structure having side walls defining a tapered internal shape with the wider proximal end of the structure being mounted on the distal flange of the injector body and the narrower distal end of the structure being left unobstructed/unattached to provide an opening for passage of an injection nozzle, and the lens support comprising a pair of parallel wedge plates of tapered shape dimensioned to be capable of abutting the side walls of the support guide when positioned within the support guide near its distal end, the parallel wedge plates being connected at their narrow extremity to the injection nozzle, and a pair of folding members pivotally connected to the wedge plates at their narrow extremity, the wedge plates and the outward pivoted folding members defining an internal support cavity that holds a flexible intraocular lens in an unfolded state, the lens support being placed within the support guide at a distance from its distal end and essentially abutting the distal flange of the injector body, c) a plunger guide disposed within the injector body with its distal end contacting the lens support, and d) a plunger inserted partially in the injector body through an opening at the proximal end of the injector body with the inserted end of the plunger being reversibly held within the plunger guide, where, in response to axial movement of the plunger over a first distance, the plunger guide and the lens support are advanced by the same distance, whereby through interaction with the tapered side walls of the support guide the folding members of the lens support are forced to pivot inward to fold the intraocular lens in a direction essentially perpendicular to the injection axis and the plunger guide acquires an alternative configuration permitting movement of the plunger within the plunger guide and where, in response to axial movement of the plunger over a second distance, the folded lens is being advanced by direct contact with the plunger through the distal end of the support cavity and the injection nozzle from which the lens emerges.

In another embodiment of the invention, the support guide comprises sloped ridges sloping toward one another from the support guide proximal end to the support guide distal end of the support guide, and whereby through interaction with the sloping ridges the folding members are forced to pivot inward to fold the intraocular lens in a direction essentially perpendicular to the injection axis.

The injector may additionally comprise an end cap fixedly put on the flange of the injector body, thereby encasing the lens support.

In a more particular embodiment of the injector according to the invention, the plunger guide is reversibly attached to and moves with the plunger when the latter is moved over the first distance whereby the lens support is advanced within the support guide, and detaches from the plunger when the latter is moved further over the second distance, the plunger then being able to move freely within the plunger guide whereby the lens is driven out of the injection nozzle.

In another embodiment of the invention, the plunger guide comprises a pair of flexible legs connected on the distal side of the plunger guide by a connecting portion, the free end of each leg comprising a stop piece, and wherein the plunger comprises clipping means, able to clip on the stop pieces when the legs are in a closed position, attaching the plunger to the plunger guide, and able to be unclipped when the legs are in an open position, detaching the plunger from the plunger guide.

In yet another embodiment of the invention, the clipping means are two opposite snap hooks able to engage on the distal edge of the stop pieces.

In yet another embodiment of the invention, the injector body comprises a first portion and a second portion, the legs of the plunger guide being in the closed position when the plunger guide is at least partly positioned within the second portion, and the legs being in the open position when the plunger guide is positioned completely within the first portion.

In yet another embodiment of the invention, the length of the second and first portion corresponds, respectively, to the first and second distance.

In yet another embodiment of the invention, the internal section of the second portion is such as to force the legs of the plunger guide to be in the closed position and the first portion has an internal section larger than the one of the second portion allowing the legs to regain their unstressed open position.

In yet another embodiment of the invention, each folding member comprises a notch at its distal extremity, the notch being able to abut against the edge of the injection nozzle in order to pivotally mount the folding member in the lens support.

In yet another embodiment of the invention, the folding members are fixed by their distal extremity to the external wall of the injection nozzle with a flexible link.

In yet another embodiment of the invention, the support guide comprises two sloped ridges destined to cooperate with the folding members, forcing them to fold until they become essentially parallel to the injection axis as the lens support is advanced within the support guide over the first distance.

In yet another embodiment of the invention, each folding member comprises a protruding element (e.g., a nose) on the side opposite to that forming the lens cavity, which element cooperates with the sloped ridges.

In yet another embodiment of the invention, a plug is held at the distal end of the plunger, the plug being able to drive the lens when the plunger is moved over the second distance.

In yet another embodiment of the invention, the plug is made from a soft and flexible material.

In yet another embodiment of the invention, the distal end of the plunger has the shape of a two-toothed fork destined to hold the plug.

In yet another embodiment of the invention, the lens support and the support guide comprise through holes destined to the filling of the internal support cavity with a viscoelastic solution.

In yet another embodiment of the invention, the end piece comprises a toric joint, the end piece being fixed sealing fluidly on the injector body and the opening being able to guide the plunger passing through it.

In yet another embodiment of the invention, the lens support is fabricated in one piece by an injection plastic molding process.

The present invention also encompasses a method for assembling are injector of the invention, the method comprising the steps of:

a) disposing tonic joint and, optionally, the end piece on the plunger and, optionally, mounting a flexible plug at the distal end of the plunger;

b) inserting the plunger into the injector body through the end piece of the injector body;

c) inserting the plunger guide within the injector body;

d) disposing the intraocular lens unfolded within the internal support cavity of the lens support, and mounting the lens support on the plunger guide;

e) fixing the support guide and the end cap on the injector body;

f) optionally introducing a sufficient volume of an aqueous solution though an opening in the end piece of the plunger to keep the lens wetted;

g) fixing toric joint and sleeve portion on the end piece of the injector body; and h) optionally packaging the injector in a sealable flexible packaging, sealing the container and sterilizing the packaged injector.

In a particular embodiment of the assembly method, in step d) a lens having two opposing haptics is disposed within the internal support cavity with the two haptics being oriented along the injection axis.

The present invention also encompasses a method for injecting an intraocular lens using an injector of the invention, comprising the steps of:
a) removing the end cap from the flange of the injector body;
b) depressing the plunger over a first distance in order to advance the lens support within the support guide and fold the lens along the injection axis; and
c) depressing the plunger over a second distance in order to drive the lens outside of the injection nozzle.

In an embodiment of the injection method, the injector is removed from its packaging during a preliminary step.

In another embodiment of the injecting method, a viscoelastic solution is introduced within the internal support cavity prior to step b) of the above-described injection method.

In yet another embodiment of the injection method, the viscoelastic solution is introduced within the internal support cavity through holes provided in wedge plates of the lens support and the support guide, respectively, or through the injection nozzle.

In the present description of the invention, the expressions "distal end" or "distal extremity" signify the end on the side of the injection, while the expression "proximal end" signifies the opposite side.

BRIEF DESCRIPTION OF THE DRAWINGS

The invention will be better understood with the aid of the description of an embodiment given by way of example and illustrated by the figures, in which:

FIG. 4 shows an isolated view of a plunger and a lens support;

FIG. 5 shows an isolated view of a lens support with wedge plate, a pair of folding members and an injection nozzle;

FIG. 6 shows another isolated view of the lens support with the pair of folding members being pivotally mounted;

FIG. 7B shows a section view along the line C-C of FIG. 7A;

FIG. 11 shows the end cap viewed from its proximal end.

DETAILED DESCRIPTION OF EMBODIMENTS OF THE INVENTION

Figure 1:
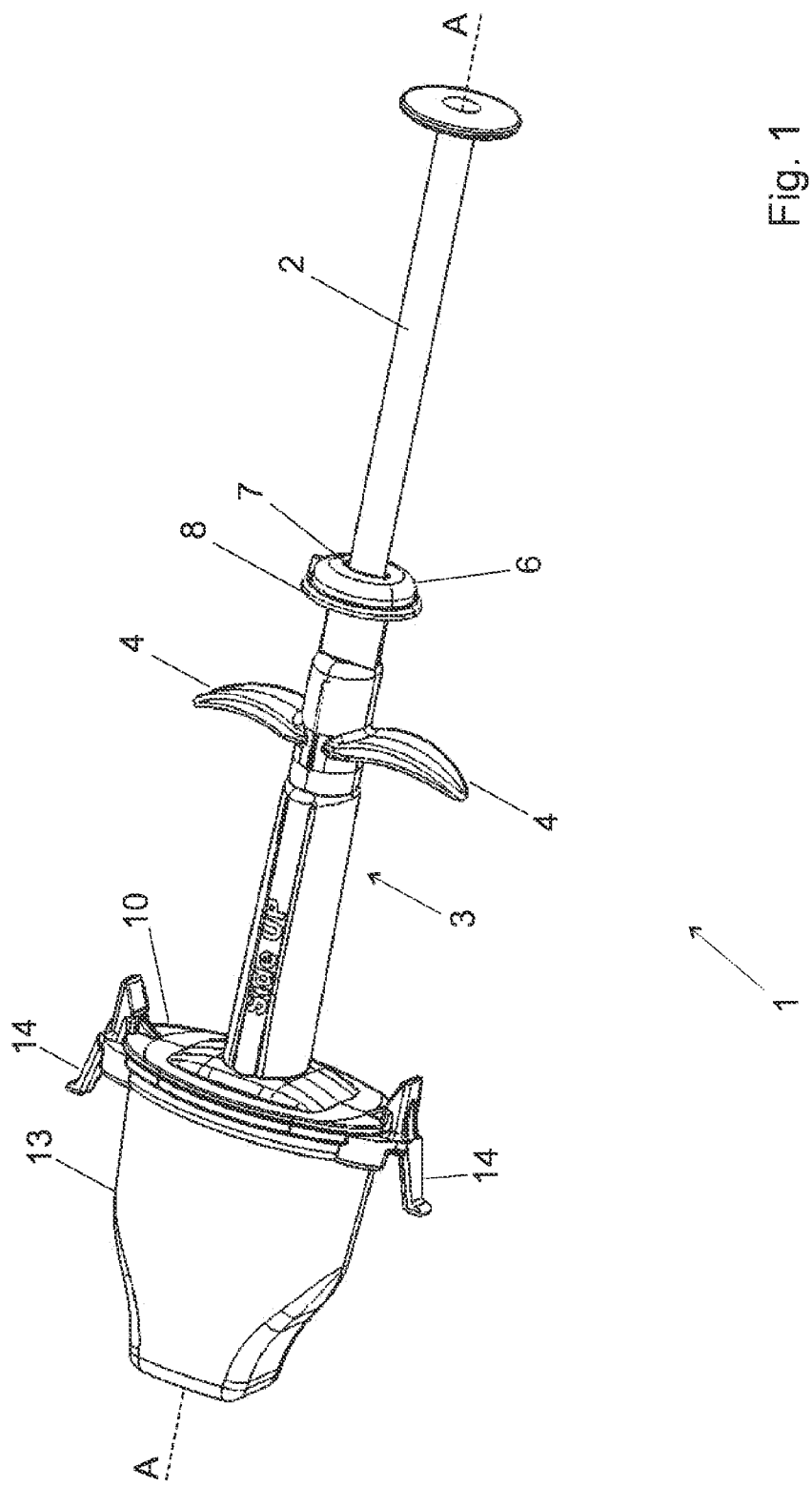
FIG. 1 represents an injector comprising an end cap, an injector body, a plunger, according to an embodiment of the invention.
Figure 2:
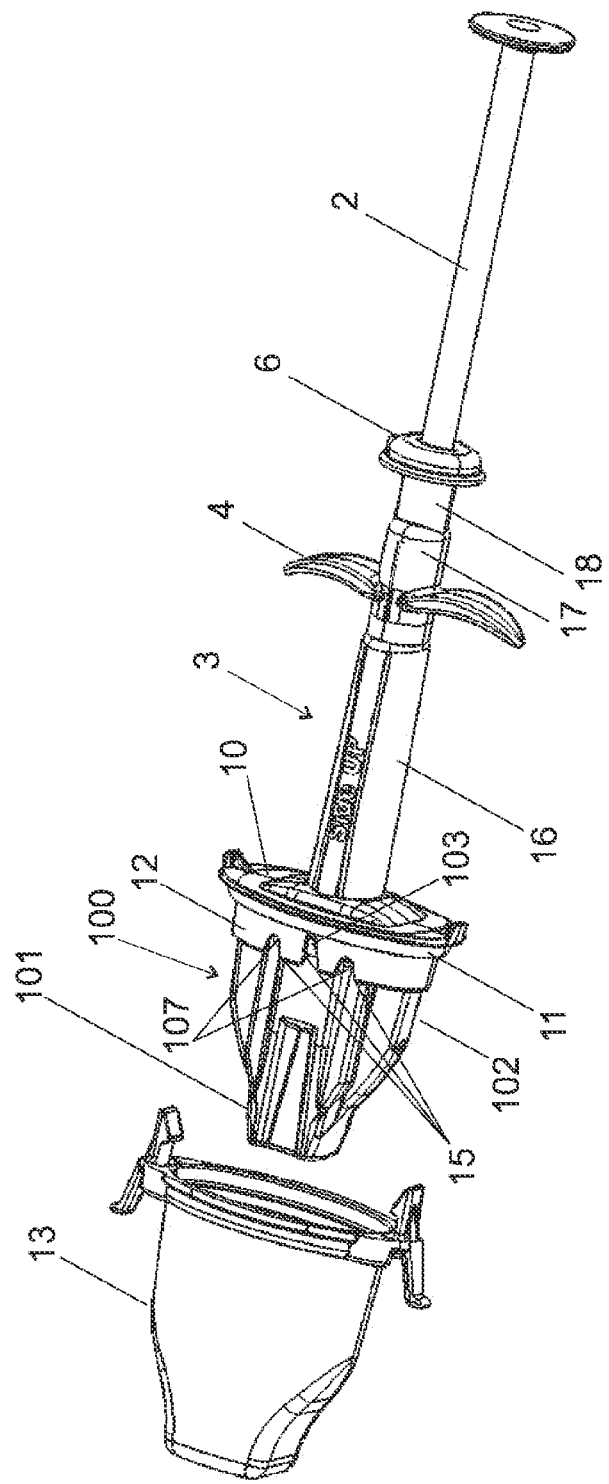
FIG. 2 represents a partial view of the injector of FIG. 1 where the end cap has been removed, showing a support guide.
Figure 3:
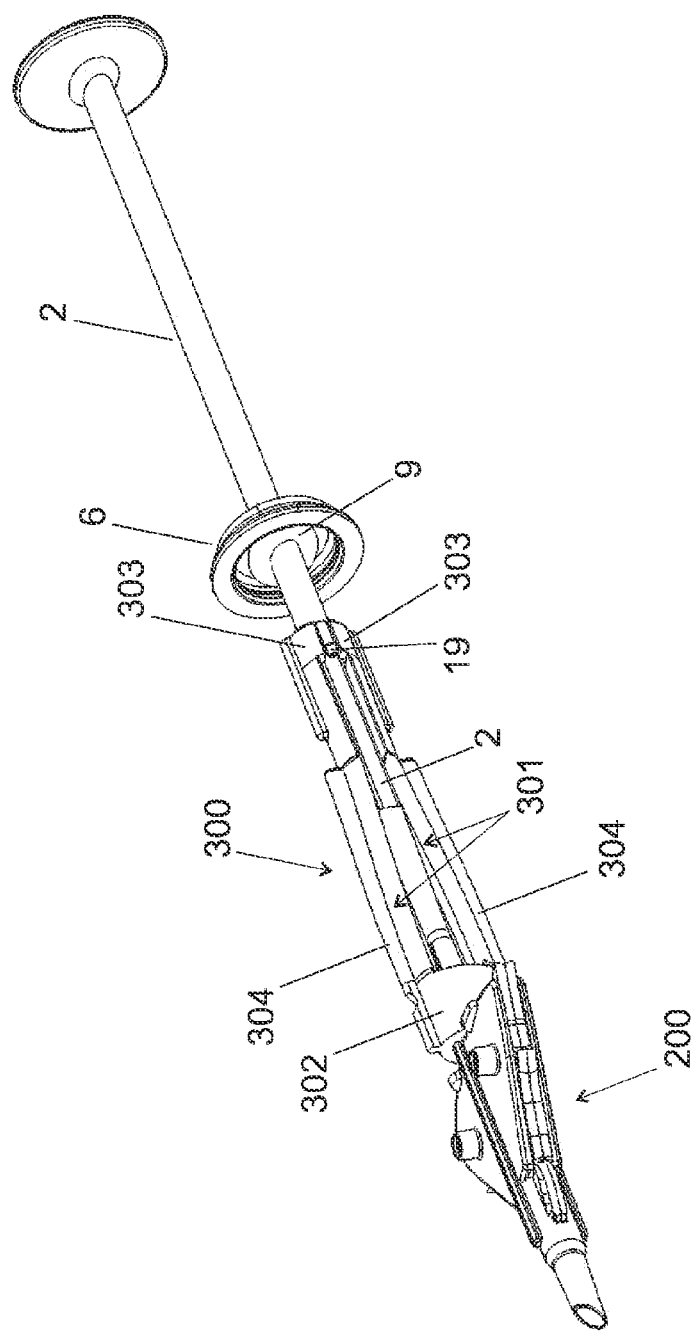
FIG. 3 represents another partial view of the injector where end cap, injector body, and support guide have been removed, showing a lens support, a plunger guide and a plunger.

An injector 1 according to an embodiment of the invention is represented in FIGS. 1, 2 and 3. The injector 1 comprises a plunger 2, extending along a longitudinal axis corresponding to the injection axis A, within a hollow cylindrical injector body 3. In the example of FIGS. 1 and 2, the injector body 3 comprises two opposite wing-shaped finger tabs 4, extending essentially perpendicular to the injection axis A and mounted on the injector body 3. Different configurations of the injector body 3 and finger tabs 4 are also possible as long as the injector body 3 is provided with means against which the fingers of a user can bear. In another example not represented, the injector body 3 can comprise two pairs of opposite finger tabs mounted on the injector body 3 on a radially extending support structure.

The injector body 3 is closed at its proximal end by an end piece 6 comprising an opening 7 in which the plunger 2 is introduced and guided. The end piece 6 has a sleeve portion 8 arranged to be fixed by snap-fit into the proximal end of the injector body 3. A first tonic joint 9 (see FIG. 3) is accommodated in the end piece 6 in order to seal fluidly the end piece 6 on the injector body 3 and the opening 7 with the plunger 2 passing through it. The tonic joint 9 may be formed of any flexible elastomeric material.

At its distal end, or at the end opposite to the end piece 6, the injector body 3 comprises an oval-shaped flange portion 10 extending essentially perpendicular to the injection axis A. Flange 10 comprises a collar portion 12 (see FIG. 2), extending in the axial direction from part 10. Other configurations of the flange 10 are also possible. For example, flange 10 can have a circular, an elliptical or a rectangular shape and can be supported on the injector body 3 with support elements (not represented).

In an embodiment of the invention, the injector body 3 comprises a first portion 16 having a first internal diameter and extending from the flange 10 to a second portion 17 having a second internal diameter that is smaller than the first internal diameter (FIG. 2). The injector body 3 also comprises a third portion 18, having an internal smaller than the one of the second portion 17, and extending between the second portion 17 and the end piece 6.

In FIG. 1, the injector 1 comprises an end cap 13 able to be fixedly put on flange 10 using two clips 14, located on opposing positions on the end cap 13 and engaging on the face of flange 10, opposed to the end cap 13, or by any other fixation means. A second tonic joint 11 (see FIG. 2) placed around the outer wall of the collar portion 12 insures the liquid tightness between the end cap 13 and flange 10.

The injector 1 also comprises a lens compartment consisting of a support guide 100 and a lens support 200 (see FIG. 3). FIG. 2 represents the injector 1 where the end cap 13 has been removed from the injector body 3, showing the support guide 100 fixed on the flange 10. The support guide 100 is an open hollow structure having side walls defining a tapered internal shape, a narrower, truncated support guide distal end 101, and a wider proximal end 102 having an oval section, or any section conformal with the internal periphery of the collar portion 12. The support guide 100 can be mounted and fixed on the flange 10 by press-fitting its proximal end 102 within the internal periphery of the collar portion 12. In the example of FIG. 2, the support guide 100 contains a guiding pin 103 fitted in a corresponding indentation 15 in the collar portion 12, insuring a better positioning and fixation of the support guide 100 on the flange 10. Holes 107 are provided in the support guide 100 in order to allow for the introduction of a viscoelastic solution within the lens support 200 as will be explained below. In the example of FIG. 2, the holes 107 are accessible through indentations 15 let into the collar portion 12.

In an embodiment of the invention, the injector body 3 is fabricated in one piece with an injection plastic molding process.

Plunger and Plunger Guide

FIG. 3 represents another partial view of the injector 1 from which the injector body 3, the end cap 13, and the support guide 100, have been removed. FIG. 3 shows the plunger 2 extending between the end piece 6, with its tonic joint 9, and the lens support 200, placed underneath the support guide 100 illustrated in FIG. 2. Also visible in FIG. 3 is a plunger guide 300, disposed within the injector body 3 and extending between the internal wall of the injector body 3 and the plunger 2. The plunger guide 300 comprises a pain of flexible legs 301 of hollow semi-oval shape, the legs 301 being connected on the distal side of the plunger guide 300, or on the side of the lens support 200, by a connecting portion 302 integrally formed with the legs 301. The legs 301 each comprise a protruding stop piece 303 at their respective free ends.

In FIG. 3, the legs 301 are shown in an unstressed open position allowing the plunger 2 to move axially within the plunger guide 300. The plunger guide 300 also comprises two opposite ribs 304, extending along its whole length. The ribs 304 are guided in corresponding grooves (not shown) provided in the internal wall of the injector body 3, when the plunger guide 300 is inserted within the injector body 3, and used to orient radially and guide axially the plunger guide 300 within the injector body 3.

FIG. 4 shows an isolated view of the plunger 2 with the lens support 200 disposed at the distal end 22 of the plunger 2. The plunger 2 has preferably an elliptical or ovoid section but can have any other suitable section shape such as a circular, square or rectangular section. The plunger 2 also comprises clipping means. In the example of FIG. 4, the clipping means are two snap hooks 19 that are oppositely disposed on the plunger 2, each at a position corresponding to that one of a stop piece 303 of the plunger guide 300.

Lens Support

The lens support 200 according to an embodiment of the invention is represented in the perspective views of FIG. 5 and FIG. 6. The lens support 200 comprises a pair of parallel wedge plates 201 of tapered shape and connected, at their narrow extremity, to an injection nozzle 202. The injection nozzle 202 is terminated by a nozzle distal end 203 destined to be introduced in an incision formed in the wall of a patient's eye during lens replacement surgery. The interior of the injection nozzle 202 forms a nozzle canal 204.

Figure 8:
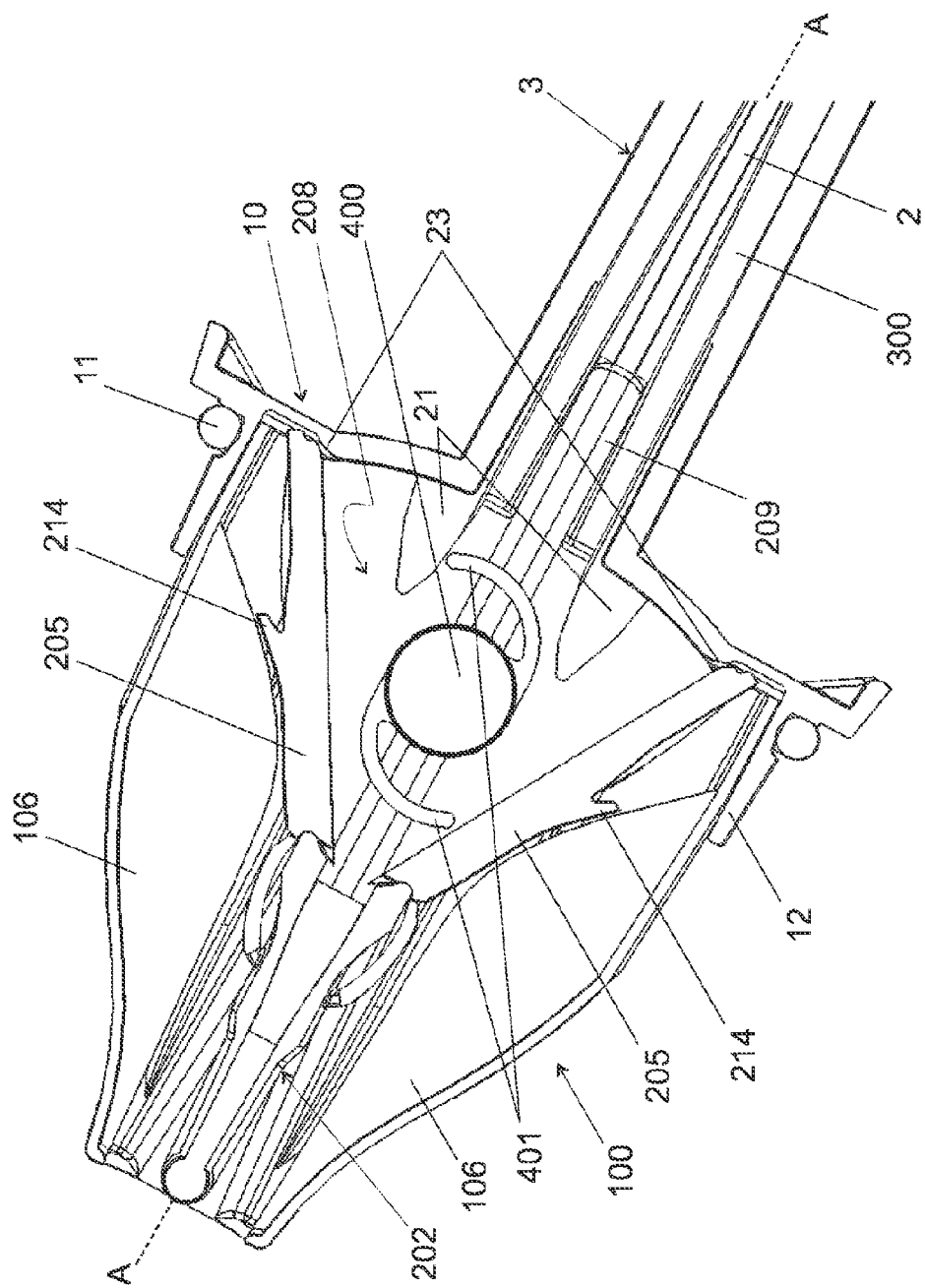
FIG. 8 shows an intraocular lens being disposed within the lens support, according to an embodiment of the invention.
Figure 9:
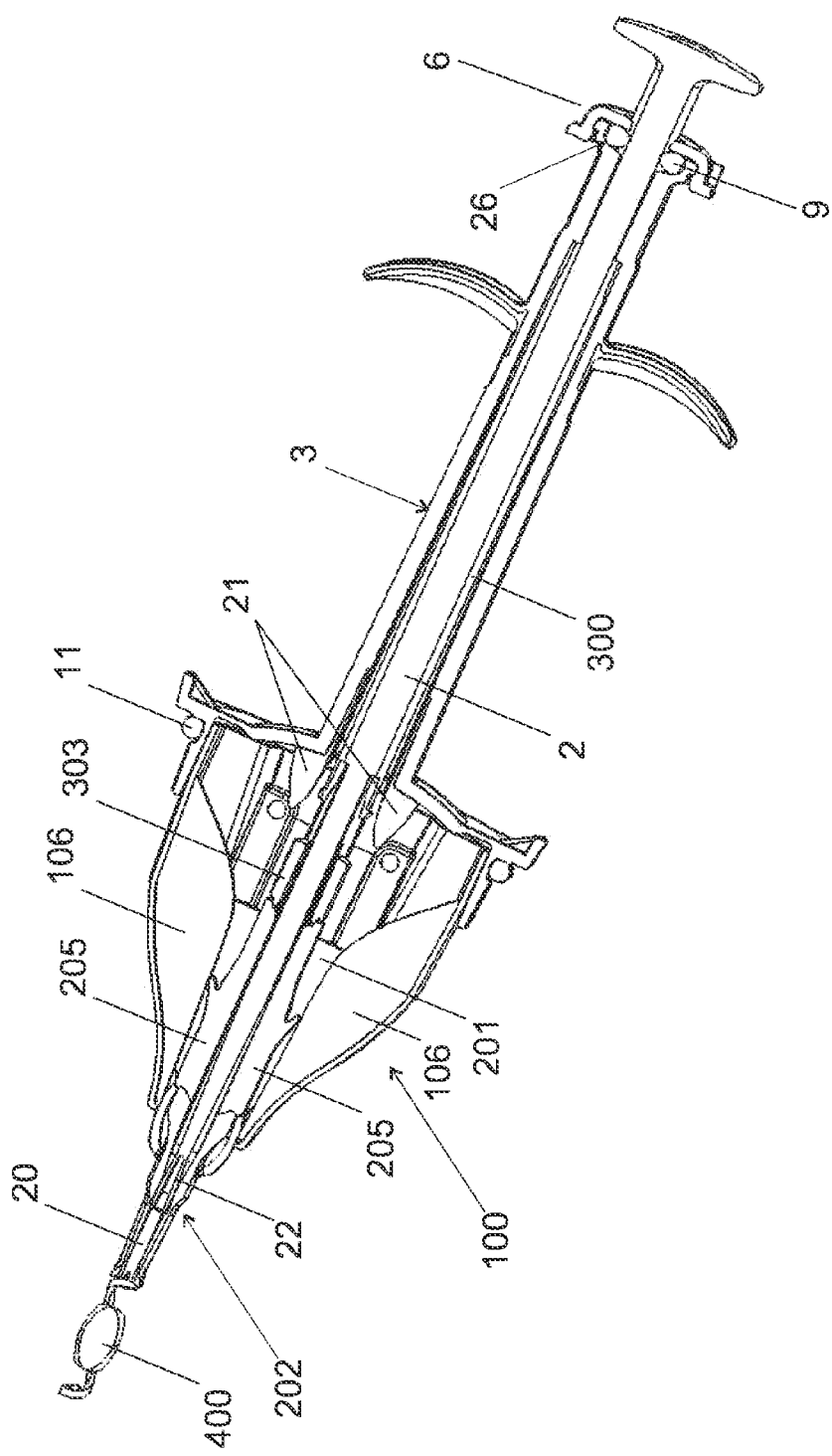
FIG. 9 illustrates the intraocular lens being completely folded within the lens support, according to an embodiment of the invention.

The lens support 200 also comprises a folding device for folding the lens 400 in a direction essentially perpendicular to the injector axis in response to axial movement of the plunger 2 as exemplified in FIGS. 8 and 9. In the example of FIGS. 5 and 6, the folding device is a pair of folding members 205 being fixed by their distal extremity, which is the extremity on the side of the injection nozzle 202, to the external wall of the injection nozzle 202 with a flexible link 206. The folding members 205 comprise a notch 207 at their distal extremity. The pair of folding members 205 can be pivotally mounted by abutting their respective notches 207 against edges of the injection nozzle 202, as shown in FIG. 6. The spacing between the two wedge plates 201 allows the folding members 205 to pivot within the two plates 201 while being guided laterally by the plates 201. When the two folding members 205 are in an open position as shown in FIG. 6, the two wedge plates 201 and the folding members 205 delimit an internal support cavity 208.

The wedges plates 201 also comprise a tail-shaped part 209, extending along the plunger 2 and within the plunger guide 300 as shown in FIG. 3. The internal surface of the tail-shaped part 209 forms a groove 210 extending along the injection axis A on the internal surface of the wedge plates 201, forming an injection canal that extends the nozzle canal 204 of the injection nozzle 202. Two ribs 211 extend along the injection axis A, on the tail-shaped part 209 and the two opposite external surfaces of the wedge plates 201 of the lens support 200.

Support Guide

Figure 7A:
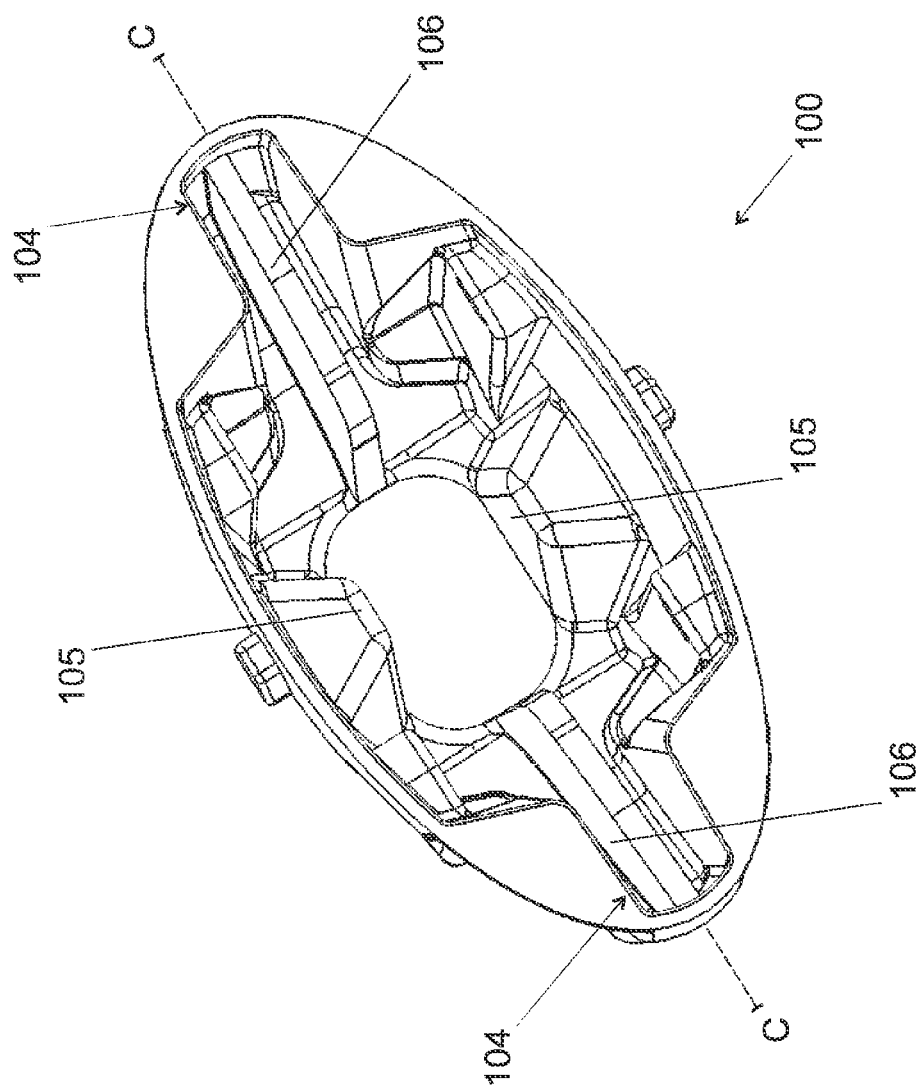
FIG. 7A shows an isolated perspective view of the lens support mounted within the support guide seen from the plunger side, according to an embodiment of the invention.

FIGS. 7A and 7B show an isolated view of the support guide 100 according to an embodiment of the invention. In FIG. 7A, the support guide 100 is seen from the plunger side, and a section view along the line C-C of FIG. 7A is represented in FIG. 7B. In FIG. 7B, the lens support 200 is also shown with pivoted folding members 205.

The support guide 100 comprises two internal lateral sloped ridges 106, formed within the internal surface of the support guide 100 and sloping toward one another from the support guide proximal end 102 to the support guide distal end 101 of the support guide 100. These sloped ridges 106 are destined to cooperate with the folding members 205 as will be explained below.

In the example of FIGS. 7A and 7B, the internal surface of the support guide 100 also comprises two guiding slots 104 extending along both sides of the support guide 100, and adapted to guide laterally the movement of the lens support 200 within the support guide 100 along the injection axis A. The two ribs 211 press against two parallel guiding faces 105, extending along the injection axis A and oppositely disposed on the internal upper and lower surfaces of the support guide 100, in order to laterally guide the lens support 200 advancing within the support guide 100. Alternatively, the two ribs 211 can also press against two parallel guide ribs (not represented), extending along the injection axis A and oppositely disposed on the internal upper and lower surfaces of the support guide 100.

Other configurations of the support guide 100 are also possible. For example, the guiding slots 104 can be replaced by a pair of ribs in order to guide laterally the movement of the lens support 200 within the support guide 100 along the injection axis A.

The lens injectors of the present invention and their various pans may fabricated from different types of plastic materials. For example, the injector body may be produced from polycarbonate (PC), polyetherimide (PEI) or polysulfone (PSU), the end cap from PC, PEI or polyamide (PA), the plunger from PC, PEI or PSU, the support guide from PP, PC, polybutylene-terephtalate (PBT) or polyoxymethylene (POM), the lens support from POM, PP, BC, PA, PEI or polyethylene-terephtalate (PET), the plunger guide from PA, PBT or polypropylene, the plug from silicone or a vulcanized thermoplastic material, and the toric joints from silicone.

Assembling the Injector

When assembling the injector 1, the end piece 6 and the toric joint 9 are first disposed on the proximal end of the plunger 2. Here, the plunger 2 is inserted into the end piece 6 through the opening 7. The plunger 2 is then inserted into the injector body 3. The two snap hooks 19 of the plunger 2 are arranged such as to be able to pass through the third portion 18 of the injector body 3, and abut against the distal end of portion 18 once the hooks 19 have passed this portion 18, preventing the plunger 2 from moving backward. Preferably, the end piece 6 is not yet clipped on the proximal end of the injector body 3.

In a preferred embodiment of the injector of the invention, a flexible plug 20 is subsequently mounted on the distal end of plunger 22. The plug 20 is preferably made from a soft and flexible material, in order to avoid scratching of the lens 400 during the injection operation. Here, the distal end of the plunger 2 can comprise a forked distal end 22, as shown in FIG. 4, allowing the flexible plug 20 to extend at least partially in between the two teeth of the distal end 22. Other configurations of the distal end 22, that abuts the plug 20, are also possible. It is noted that plug 20 may be added to the plunger end 22 at a later stage, but prior to the mounting of the lens support 200 on the plunger guide 300.

The plunger guide 300 is next mounted within the injector body 3. The two opposite ribs 304 of the plunger guide 300 are guided within the corresponding grooves of the injector body 3 allowing the plunger guide 300 to be introduced into the desired angular position within the injector body 3. When the plunger guide 300 reaches its full rear position, it is forced into its closed position, the clipping means of the plunger 2, here the two snap hooks 19, are able to engage on the distal edge of the stop pieces 303, reversibly connecting the plunger guide 300 and the plunger 2.

The respective internal diameters of the portions 16, 17, 18 are such as to allow the plunger guide 300 to be introduced within the first and second portions but not within the third portion 18. The plunger guide 300 introduced within the injector body 3 from the flange 10 side thus abuts against the end of the second portion 17, adjacent to the third portion 18. In this initial position, the plunger guide 300 extends along the first and second portions 16, 17. The internal diameter of the second portion 17 is such as to force the two opposite stop pieces 303 of the legs 301 to come in contact with the two snap hooks 19, the plunger guide 300 being thus in a closed position. When, in response to a forward movement of the plunger, the plunger guide is advanced out of the second portion 17 and into the first portion 16, the plunger guide 300 is able to regain its unstressed open position.

Other configurations of the injector body 3 are also possible, as long as they provide a configuration that enables the plunger guide 300 to be either in a closed position or in an unstressed open position, depending on the axial position of the plunger guide 300 within the injector body 3. For example, the injector body 3 can have a uniform internal diameter along its whole length but comprise internal ribs distributed around its internal wall, the ribs having a height that varies between sections along the injector body 3.

An intraocular lens 400 is then disposed unfolded between the two wedge plates 201, within the internal support cavity 208 (FIG. 6; FIG. 8). Preferably, the lens 400 is disposed within the internal support cavity 208 with their two haptics 401 being oriented along the injection axis A, as shown in FIG. 8.

The lens support 200 containing the lens 400 is then mounted on the plunger guide 300 by inserting the tail-shaped part 209 within the connecting portion 302 of the plunger guide 300 (FIG. 3; FIG. 6). In this position, the two folding members 205 are prevented from pivoting on the intraocular lens 400 by abutting against two protrusions 23 located on the flange 10 of the injector body 3 (see FIG. 8). Also shown in FIG. 8 are two protruding members 21 arranged to maintain the unfolded lens 400 within the lens support 200 in its unfolded orientation as described above, until the lens 400 is folded and ejected. The protruding members 21 do not prevent the pivoting of the two folding members 205.

The support guide 100 is then fixed on flange 10 of the injector body 3 and the end cap 13 is clipped on the flange 10 after placing the second toric joint 11 around the external periphery of the collar portion 12 (FIG. 1; FIG. 2). The second toric joint 11 could also be placed at any other injector assembly steps, before the step of clipping the end cap 13 on the flange 10, described below.

Figure 10:
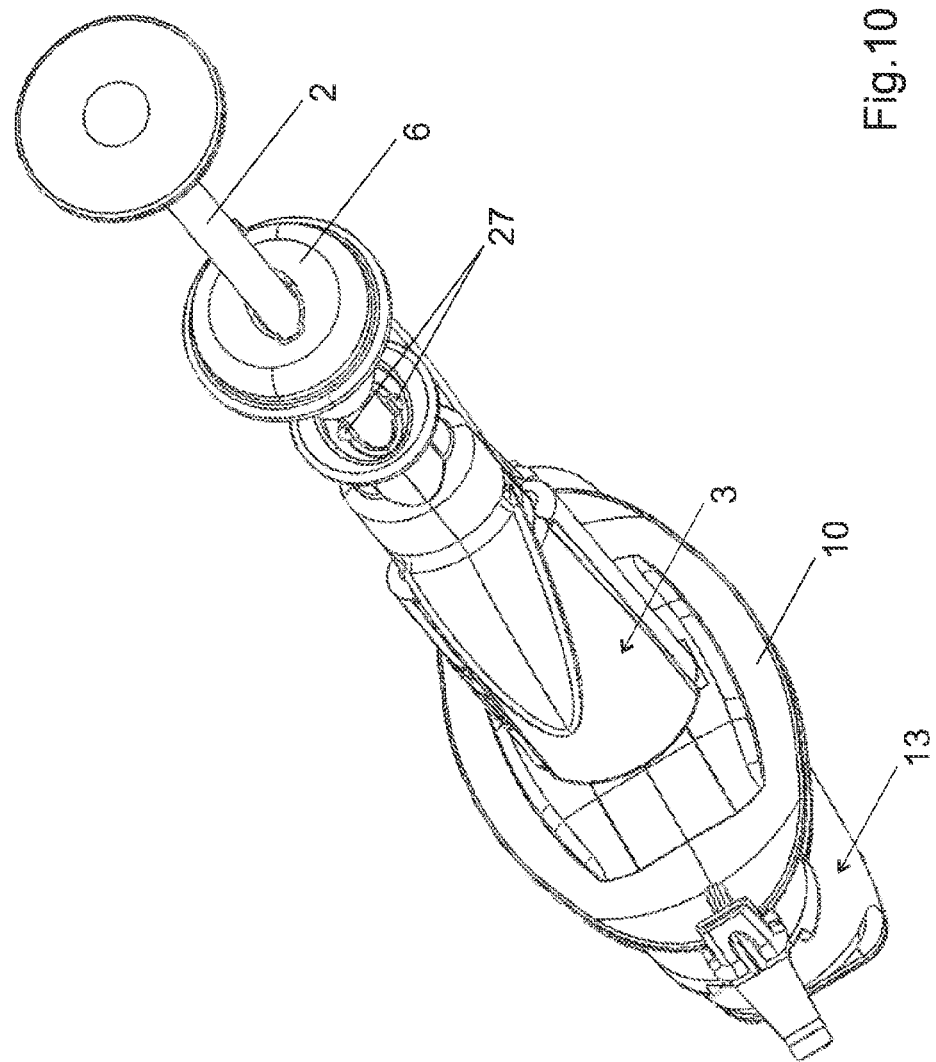
FIG. 10 represents the injector of the invention, viewed from its proximal end.

In the case of a flexible hydrophilic intraocular lens, the end cap 13 and the injector body 3 are filled with an aqueous solution such as a saline solution, distilled water, or any other aqueous solution adequate for keeping the intraocular lens 400 wet. The aqueous solution may be introduced through filling openings, in the proximal end of the injector body 3 by means of a syringe. Such two openings 27 are shown in the example of FIG. 10 representing the injector 3 viewed from its proximal end.

The aqueous solution fills at least partly the volume enclosed by the end cap 13, lens support 200 and injector body 3. In the case a flexible hydrophobic intraocular lens is used, there is no need for a bathing solution and the step of filling the injector body 3 and the end cap 13 with an aqueous solution may be omitted.

When the end cap 13 is fixed on the injector body 3, the lens support 200 abuts against the end cap 13 and the plunger 2 cannot be depressed.

In a preferred embodiment of the invention shown in see FIG. 11 representing the end cap 13 viewed from its proximal end, the end cap 13 comprises a central hollow tube 24 extending along the injection axis A toward the injector body 3. When the end cap 13 is fixed on the injector body 3, the distal end 215 of both opposite support ribs 211 of the lens support 200 abuts against the proximal end 25 of the central tube 24. In this configuration, the plunger 2 cannot be moved backward due to the snap hooks 19 abutting against the distal end of portion 18, as described above. Consequently, any false manipulation of the plunger 2 prior to the injection operation is avoided.

After fixing the end cap 13, the toric joint 9 is placed on a grove 26 on the proximal end of the injector body 3 (see FIG. 9) and the end piece 6 is clipped on said proximal end, making the interior of the injector body sealed. The injector 1 is then ready to be packaged into a sealable flexible packaging (not represented) such as a sleeve or blister, or any other packaging. After the packaging is sealed, the packaged injector 1 is subjected to sterilization. A preferred method of sterilization is steam sterilization (autoclaving).

Using the Injector

Prior to the injection operation, the injector is separated from its packaging, and the end cap 13 is unclipped and removed from the flange 10, causing the aqueous solution to drain from the injector body 3 and the lens support 200. In order to keep the lens 400 and lens support 200 lubricated during the injection operation, a viscoelastic solution such as a solution containing hyaluronic acid, chondroitin sulfate or a cellulose derivative such as hydroxypropylmethylcellulose (EIPMC) can be introduced within the internal support cavity 208 through holes 212 provided in the wedge plates 205 and the corresponding holes 107 of the support guide 100, for example, by using a syringe. Alternatively or in addition, the viscoelastic solution can also be introduced through the nozzle distal end 203 of the injection nozzle 202. The holes 107 and 212, and the nozzle distal end 203 also increase the fluidic communication within the end cap 13, facilitating the penetration of aqueous wetting solution into the lens support 200.

During an injection operation, the plunger 2 is depressed causing the plunger guide 300 to move forward over a first distance, advancing the lens support 200 within the support guide 100 along the injection axis A. During the advance of the lens support 200, the sloped ridges 106 of the support guide 100 force the pair of folding members 205 to pivot toward the injection axis A, drawing them near to one another until they become essentially parallel to the injection axis A, transforming the internal support cavity 208 into an injection canal 213 that extends along the folded folding members 205 and into the nozzle canal 204 of the injection nozzle 202. The lens support 200 advances in the support guide 100 until it abuts against the support guide 100 and cannot advance further.

In an embodiment of the invention not represented, during the advance of the lens support 200 within the support guide 100, the folding members 205 of the lens support 200 interact with the internal tapered side walls, forcing the folding members 205 to pivot inward and fold the intraocular lens in a direction essentially perpendicular to the injection axis A.

The above operation causes the intraocular lens 400 to fold, the lens 400 being folded or rolled in a direction essentially perpendicular to the injection axis A as shown in FIG. 7B, when completely folded. Consequently, the folded lens 400 is ready to be advanced axially into the nozzle canal 204.

In an embodiment of the invention, each folding member 205 comprises a protruding element 214. When the lens support 200 advances within the support guide 100, the sloped ridges 106 press against the protruding elements 214, and pivots the pair of folding members 205 toward the injection axis A, as described above. The protruding elements 214 can advantageously enhance the angular distance the folding members 205 will travel within the lens support 200 during the forward motion of the lens support within the support guide 100. Moreover, the use of protruding elements 214 can also reduce the friction during the advancement of the lens support 200 within the support guide 100, compared to a contact made along the whole folding member 205.

When the plunger 2 has moved over the first distance and the lens support 200 reached its abutting position within the support guide 100, the plunger guide 300 has moved completely outside the second portion 17 and extends only within the first portion 16 of the injector body 3 and within the support guide 100. It is noted that once plunger guide 300 has moved outside of second portion 17, it cannot be returned to its initial position within portion 17, thereby preventing an unfolding of the folded lens as a consequence of an accidental retraction of plunger 2. The diameter of the first portion 16 is large enough to allow the two legs 301 of the plunger guide 300 to regain their unstressed position, in which the two legs 301 are slightly bent apart, enabling the plunger guide 300 to be detached from the plunger 2, allowing the plunger 2 to move freely within the plunger guide 300 and advance within it.

When operator pressure continues to be applied, the plunger 2 and plug 20 advance over a second distance and propel the folded lens 400 along the injection canal 213, and outside the nozzle distal end 203, enabling the lens 400 to be injected into the patient's eye (see FIG. 9). The flexible plug 20 is able to follow conformably the varying dimensions of the internal support cavity 208 formed by the two folding members 205 and the nozzle canal 204, avoiding the necessity of requiring accurate dimensions for the different parts forming the compressed support cavity 208 and the nozzle canal 204.

In an exemplary embodiment of the invention, the lens support 200 is able to advance in the support guide 100 over a distance of about 15 mm, this distance corresponding to the length of the second portion 17 of the injector body 3.

Here, the total length formed by the first and second portions 16, 17 corresponds essentially to the length of the plunger guide 300.

In an embodiment of the invention, the lens support 200, comprising the two wedge plates 201, the injection nozzle 202, the two folding, members 205 and links 206, is fabricated in one piece by an injection plastic molding process.

SYMBOLS AND REFERENCES 1 injector
2 plunger
3 injector body
4 finger tab
6 end piece
7 opening
8 sleeve portion of the end piece
9 tonic joint
10 flange
11 second toric joint
12 collar portion
13 end cap
14 clip
15 indentations
16 first portion
17 second portion
18 third portion
19 snap hook
20 plug
21 protruding member
22 distal end of the plunger
23 protrusions
24 central hollow tube
25 proximal end of the central tube
26 groove
27 filling opening
100 support guide
101 support guide distal end
102 support guide proximal end
103 guiding pin
104 guiding slot
105 guide ribs
106 sloped ridge
107 holes in the support guide
200 lens support
201 wedge plate
202 injection nozzle
203 nozzle distal end
204 nozzle canal
205 folding member
206 link
207 notch
208 internal support cavity
209 tail-shaped part
210 groove
211 support rib
212 holes in the wedge plates
213 injection canal
214 protruding element
215 distal end of support rib
300 plunger guide
301 legs of the plunger tilde
302 connecting portion
303 stop piece
304 rib
400 intraocular lens
401 haptic
A injection axis

The invention claimed is:

1. An injector for folding and injecting into an eye of a patient a flexible intraocular lens, the injector comprising:
   an injection nozzle;
   a support guide around the injection nozzle;
   a lens support having a plate and a pair of folding members, each folding member having a first end attached to the injection nozzle and a second end;
   a lens compartment in communication with the injection nozzle; and
   an injector body communicating with the lens compartment and a plunger that is inserted in a free end of the injector body, the plunger extending through the injector body,
   wherein each folding member pivots about an axis that is perpendicular to a longitudinal direction of the injector body, and
   wherein, upon movement of the plunger, the support guide presses the second end of each folding member inward toward a longitudinal axis of the plunger to compress a lens.

2. The injector according to claim 1 wherein the lens compartment is integrated in the injector body.

3. The injector according to claim 1, wherein the injector comprises an end cap fixedly put on a distal flange of the injector body, thereby encasing the lens support.

4. The injector according to claim 1, wherein the support guide comprises two sloped ridges destined to cooperate with the folding members, forcing the folding members to fold until they become essentially parallel to the longitudinal axis of the plunger.

5. The injector according to claim 4, wherein each folding member comprises a protruding element cooperating with the sloped ridges.

6. The injector according to claim 1, wherein the lens support and the support guide comprise through holes destined to the filling of an internal support cavity with a viscoelastic solution.

7. The injector according to claim 1, further comprising an end piece on the injector body, the end piece having an opening,
   wherein the end piece comprises a tonic joint, the end piece being fixed sealing fluidly on the injector body and the opening being able to guide the plunger passing through it.

8. A method for injecting an intraocular lens using an injector according to claim 1 and comprising the steps of:
   a) removing an end cap from a distal flange of the injector body;
   b) depressing the plunger over a first distance in order to advance the lens support within the plunger guide and fold the lens along the longitudinal axis (A); and
   c) depressing the plunger over a second distance in order to drive the lens outside of the injection nozzle.

9. The method according to claim 8, wherein the injector is removed from its packaging during a preliminary step.

10. The method according to claim 8, wherein a viscoelastic solution is introduced within the lens compartment prior to step b).

11. An injector for folding and injecting into an eye of a patient a flexible intraocular lens, the injector comprising:
    an injection nozzle;
    a support guide around the injection nozzle;
    a lens support in the support guide;
    an injector body communicating with the support guide;
    a plunger inserted in a free end of the injector body; and
    a plunger guide disposed within the injector body with its distal end contacting the lens support, the plunger movable in a longitudinal direction of the injector body,
    wherein the plunger guide is reversibly attached to and moves in the longitudinal direction of the injector body with the plunger when the plunger is moved over a first distance in the longitudinal direction of the injector body whereby the lens support is advanced within the support guide, and detaches from the plunger when the plunger is moved further over a second distance in the longitudinal direction of the injector body, the plunger being able to move freely within the plunger guide.

12. The injector according to claim 11, wherein the plunger guide comprises a pair of flexible legs connected on a distal side of the plunger guide by a connecting portion, a free end of each leg comprising a stop piece, and
    wherein the plunger comprises clipping means, able to clip on the stop pieces when the legs are in a closed position, attaching the plunger to the plunger guide, and able to be unclipped when the legs are in an open position, detaching the plunger from the plunger guide.

13. The injector according to claim 12, wherein the clipping means are two opposite snap hooks able to engage on distal edges of the stop pieces.

14. The injector according to claim 12, wherein the injector body comprises a first portion and a second portion, the legs of the plunger guide being in the closed position when the plunger guide is at least partly positioned within the second portion, and the legs being in the open position when the plunger guide is positioned completely within the first portion.

15. The injector according to claim 14, wherein a length of the second and first portion corresponds, respectively, to the first and second distance.

16. The injector according to claim 14, wherein an internal section of the second portion is such as to force the legs of the plunger guide to be in the closed position and the first portion has an internal section larger than the one of the second portion allowing the legs to regain their unstressed open position.

17. The injector according to claim 11, wherein a plug is held at a distal end of the plunger, the plug being able to drive the lens when the plunger is moved over the second distance.

18. The injector according to claim 17, wherein the plug is made from a soft and flexible material.

19. The injector according to claim 17, wherein the distal end of the plunger has a shape of a two-toothed fork destined to hold the plug.

20. The injector according to claim 11, wherein the plunger guide extends in a longitudinal direction of the injector body and is spaced from the plunger in a radial direction.

21. An injector for folding and injecting into an eye of a patient a flexible intraocular lens, the injector comprising:
    an injection nozzle;
    a support guide around the injection nozzle;
    a lens support having a pair of parallel plates and a pair of folding members, each folding member attached at an end of one of the pair of parallel plates;
    a lens compartment in communication with the injection nozzle; and
    an injector body communicating with the lens compartment and a plunger that is inserted in a free end of the injector body; the plunger extending through the injector body;

wherein the support guide presses the pair of folding members inward toward a longitudinal axis of the plunger to compress a lens, wherein the support guide comprises two sloped ridges destined to cooperate with the pair of folding members, forcing the pair of folding members to fold until they become essentially parallel to the longitudinal axis of the plunger, and wherein the sloped ridges force the folding members to be between the pair of parallel plates.

* * * * *